(12) United States Patent
Jelten

(10) Patent No.: US 6,382,219 B1
(45) Date of Patent: May 7, 2002

(54) TOOTH FLOSSING DEVICE

(76) Inventor: Jeffery A. Jelten, 920 Capitola Ave. #56, Capitola, CA (US) 95010

( * ) Notice: Subject to any disclaimer, the term of this patent is extended or adjusted under 35 U.S.C. 154(b) by 0 days.

(21) Appl. No.: 09/735,128

(22) Filed: Dec. 12, 2000

Related U.S. Application Data

(63) Continuation-in-part of application No. 09/474,825, filed on Dec. 29, 1999, which is a continuation-in-part of application No. 09/328,872, filed on Jun. 8, 1999, now abandoned.

(51) Int. Cl.[7] ................................................. A61C 15/00
(52) U.S. Cl. ........................ 132/323; 132/324; 132/325
(58) Field of Search ................................. 132/323, 324, 132/325, 326, 327, 328, 329

(56) References Cited

U.S. PATENT DOCUMENTS

| | | | | |
|---|---|---|---|---|
| 3,378,017 A | * | 4/1968 | Stiles | 601/139 |
| 4,041,962 A | * | 8/1977 | Johansson et al. | 132/323 |
| 4,616,667 A | * | 10/1986 | Tang | 132/323 |
| 5,016,660 A | * | 5/1991 | Boggs | 132/323 |
| 5,337,436 A | * | 8/1994 | Saxer et al. | 15/104.94 |

* cited by examiner

*Primary Examiner*—John J. Wilson
*Assistant Examiner*—Robyn Kieu Doan
(74) *Attorney, Agent, or Firm*—Jeffrey A. Hall

(57) ABSTRACT

A dental flossing device has a handle element with a forked end with spaced prongs. A tensioning cleat is mounted on the handle element for positioning and securing a length of dental floss and may include a trigger arm mechanism for advancing a strand of floss. A soft elastomer protective bite element is secured to the forked end of the handle element. The soft elastomer protective bite element has a top surface with a notch therein sized to secure a length of dental floss and a channel positioned underneath the floss held in the notch to allow initial penetration of floss between teeth and is resilient enough to allow further penetration when bitten down upon. The handle element includes a groove on both spaced prongs. The soft elastomer protective bite element may have a curved surface with a pair of spaced finger elements.

18 Claims, 2 Drawing Sheets

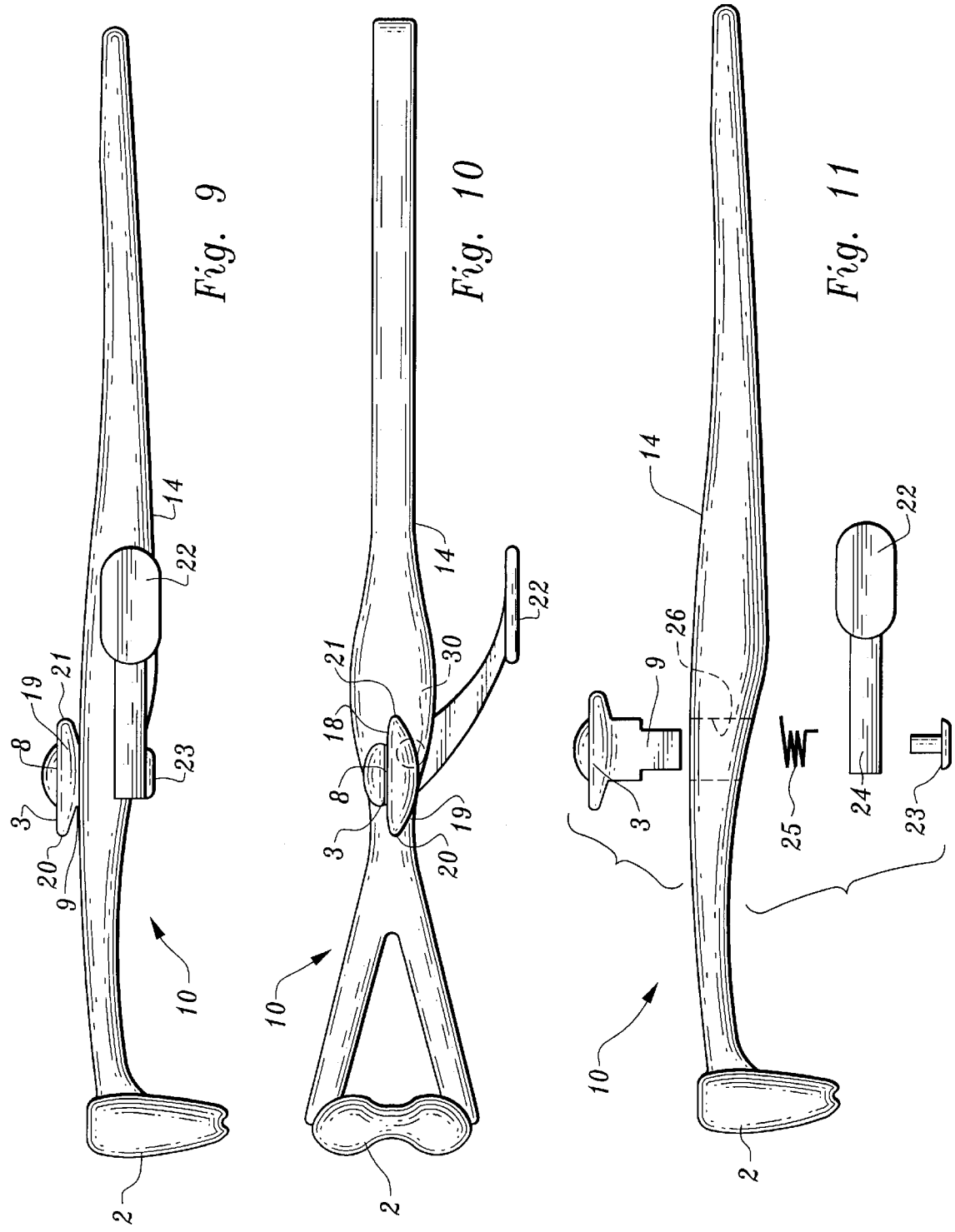

TOOTH FLOSSING DEVICE

CROSS-REFERENCE TO RELATED APPLICATIONS

This application is a continuation-in-part of and claims priority from co-pending U.S. patent application Ser. No. 09/474,825 filed Dec. 29, 1999 which is a continuation-in-part of U.S. patent application Ser. No, 09/328,872, filed Jun. 8, 1999 now abandoned.

BACKGROUND OF THE INVENTION

1. Field of Invention

This invention relates to dental flossing devices and more particularly to dental flossing devices with bite elements for driving dental floss through spaces between teeth.

2. Description of the Related Art

Heretofore, numerous devices have been proposed and implemented for use with dental floss and for aiding cleaning the spaces between teeth with dental floss. In recent years different types of dental flossing devices have been introduced. Typically the device comprise a frame have a fork shaped member for supporting a length of floss between the fork elements which is either hand operated or motor driven. Although useful for some applications, such devices are severely limited due to frequent breakage of the dental floss, discomfort, and difficulty driving the dental floss through gaps in the teeth which results in overall inefficiency.

Accordingly, the present invention provides a novel device which enables a person to easy, quickly, and comfortably floss teeth with out having to stick his or her fingers or hand in the mouth, and which is pleasant and efficient to use. The device of the present invention is portable, lightweight, inexpensive to manufacture, and highly efficient at cleaning the spaces between teeth with dental floss.

Additional objects and advantages of the invention will be set forth in the description which follows, and in part will be obvious from the description, or may be learned by practice of the invention. The objects and advantages of the invention may be realized and obtained by means of the instrumentality's and combinations particularly pointed out in the appended claims.

BRIEF SUMMARY OF THE INVENTION

The present invention is a safe and reliable dental flossing device which is held in the hand and operates by the user gently biting down on the device to work a piece of dental floss between the teeth. The device allows flossing without the need to put any fingers or hand portion in the mouth. The configuration of the device is such that all points of contact with teeth and gums are with a rounded, soft biting surface. The biting surface is provided as a protective element mounted on the end of a toothbrush type handle. The protective element may be made separate from the more ridged, plastic handle, and then snapped together to keep costs at a minimum and to simplify cleaning and replacement. Alternatively, the protective element may be molded over and/or around a toothbrush type handle as one piece. A multi-functional tensioning cleat and trigger device may be provided for control and positioning of dental floss.

Accordingly a dental flossing device is provided with a handle element, preferably with a forked end with spaced prongs. Tensioning cleat means are mounted on the handle element for positioning and securing a length of dental floss. A protective element is secured to the forked end of the handle element. The bite element has a top surface with a notch therein sized to secure a length of dental floss and a channel positioned underneath the floss held in the notch to accommodate the tooth. The handle element includes a groove on both spaced prongs. The protective element may have a curved surface with a pair of spaced finger elements.

BRIEF DESCRIPTION OF THE DRAWINGS

The accompanying drawings, which are incorporated in and constitute a part of the specification, illustrate a preferred embodiment of the invention and, together with a general description given above and the detailed description of the preferred embodiment given below, serve to explain the principles of the invention.

FIG. 9 shows a side view of another embodiment of such device with a multi-functioning tensioning cleat and trigger device, according to the invention.

FIG. 10 shows a top view of the embodiment of such device with a multi-functioning tensioning cleat and trigger device, according to the invention.

FIG. 11 shows an exploded view of the embodiment of such device with a multi-functioning tensioning cleat and trigger device, according to the invention.

DETAILED DESCRIPTION OF THE INVENTION

Reference will now be made in detail to the present preferred embodiments of the invention as illustrated in the accompanying drawings.

In accordance with the present invention, there is provided a dental flossing device with a handle element, preferably with a forked end with spaced prongs. A tensioning cleat, or multi-functional tensioning cleat is mounted on the handle element, for positioning and securing a length of dental floss. A trigger element may be included for advancing and securing the floss in position. A protective element is secured to the forked end of the handle element, and is preferably composed of a soft elastomer. The protective element has a top surface with a notch therein sized to secure a length of dental floss and a channel positioned underneath the floss held in the notch to accommodate the tooth. The handle element includes a groove on both spaced prongs. The protective element may have a curved surface with a pair of spaced finger elements.

Figure 1:
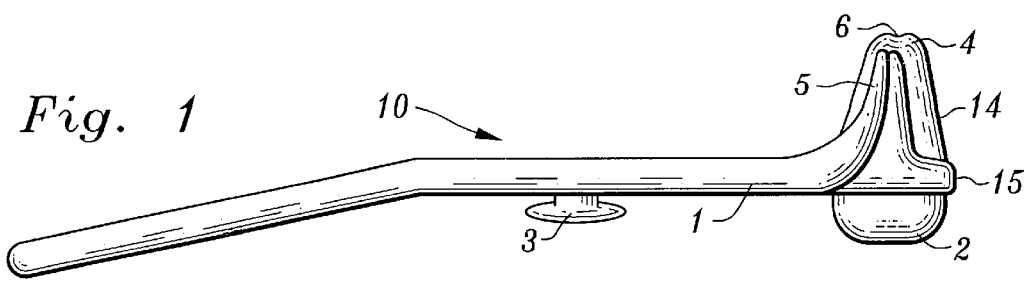
FIG. 1 is a side view of the dental flossing device, according to the invention.
Figure 3:
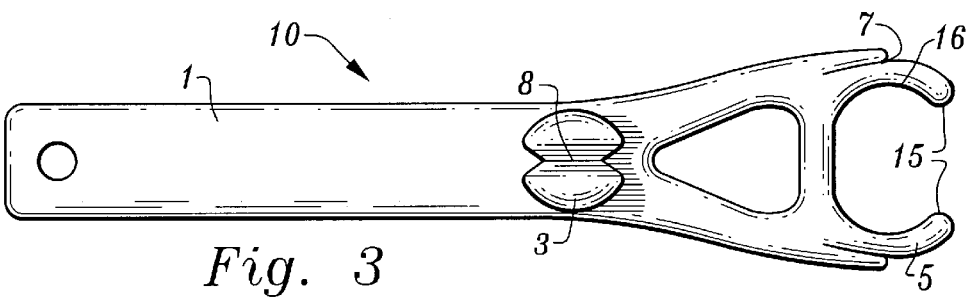
FIG. 3 shows a bottom view of such device, according to the invention.

In FIG. 1, a dental flossing device 10, for cleaning in between teeth and gums, is shown according to a preferred embodiment of the invention. Flossing device 10, includes a handle 1, which may be configured similar to a toothbrush handle and having a forked end 15, which may have an inward curvature 16, as seen in FIG. 3. Handle 1 may be made out of plastic, or other durable, resilient material. A biting element or soft elastomer bite protective element 2 is seen secured in forked portion 15 of handle 1. Protective element 2 is preferably composed of a soft elastomer protective material, which is durable and resilient, such as silicone rubber which is comfortable for biting down on. Protective element 2, protects the teeth and gums from pain and damage when biting down during flossing operations. This soft portion, allows for the user to chew on the device without damaging teeth and gums. Protective element 2 is configured to fit within forked end 15 and may be easily placed in or removed from in between the forks or prongs 5.

Figure 4:
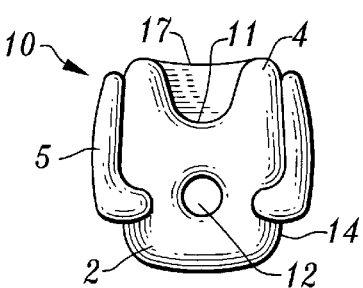
FIG. 4 shows a end view of such device, according to the invention.
Figure 8:
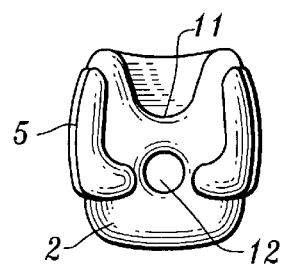
FIG. 8 shows another embodiment of such device where the prongs are molded together with the biting element, according to the invention.

Preferably the soft elastomer bite protective element 2 is configured with fingers 4, best seen in FIGS. 1, 4, and 8, which extend above ridged plastic prongs 5. A groove 6 is positioned on the upper surface of fingers 4 for positioning and securing a length of dental floss 17. A groove 7 is provided down the sides of forks or prongs 5, which guides dental floss 17 down handle 1 to notch 8 in tensioning cleat 3.

Figure 2:
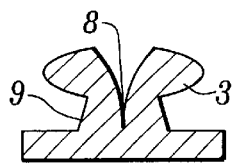
FIG. 2 is a cut-away view of the tensioning cleat of such device, according to the invention.

As seen in FIGS. 2 and 3, tensioning cleat 3 includes vertical notch or slit 8 which cuts through cleat 3 fore and aft, creating two sides of the cleat, side 18, and 19, allowing dental floss to be wedged in notch or vertical slit 8 so as to be held and positioned in cleat 3 while adjustments are made, and then locked in to cleat 3 by winding the floss around the preferably inwardly curved base 9 of cleat 3. Notch or slit 8 is important as the vertical orientation of the notch or slit allows for locking floss securing in the cleat.

With reference now to FIG. 3, a bottom view of handle 1 is shown with tensioning cleat 3 and groove 7, on fork elements 5, and an inward curvature 16 of prongs or fork elements 5, which allows biting element 2 to be snapped in and out of the prongs or fork.

In FIG. 4, an end view of flossing device 10 is shown with biting element 2 held in prongs 5. A channel or notch 11 provides a space below floss 17 when floss 17 is strung across fingers 4 of biting element 2 to allow initial penetration of the floss between teeth. An reverse curve 12 or valley is preferably included in the heel of protective element 2, best seen in FIGS. 4 and 8, and is preferably provided in protective element 2 to prevent the users teeth from sliding off when biting.

Figure 5:
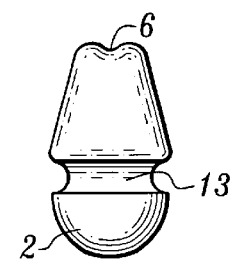
FIG. 5 shows a side view of the biting element of such device, according to the invention.

With reference to FIG. 5, a notch or channel 13 is preferably provided on the side of protective element 2 to plug handle 1 into. Preferably notch 13 continues around the entire circumference of biting element 2, so that handle 1 may be attached from either side of protective element 2.

Figure 6:
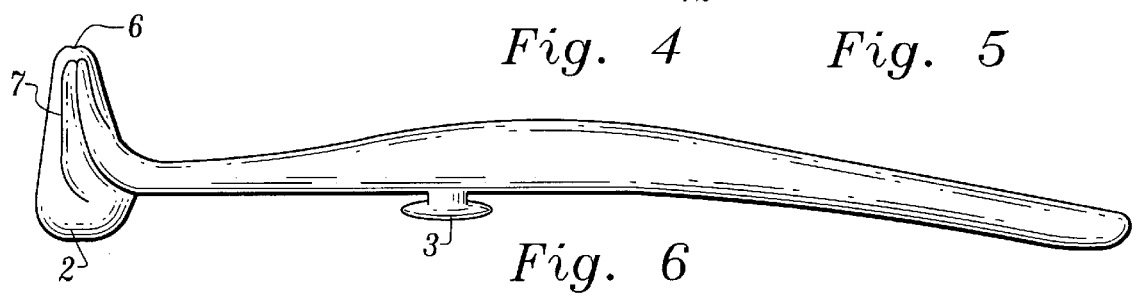
FIG. 6 shows a top view of such device where a flattened type handle is used, according to the invention.
Figure 7:
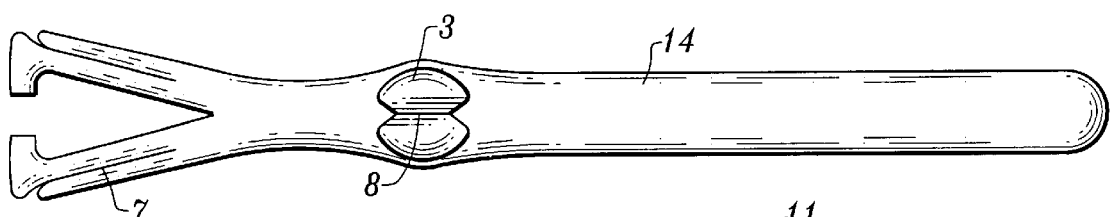
FIG. 7 shows a side view of such device where a raised or curved type handle is used, according to the invention.

In FIGS. 1 and 3, and in FIGS. 6 and 7, two different embodiments of dental flossing device 10 are shown. In FIGS. 1 and 3 a flattened type handle 14 is used, while in FIGS. 6 and 7, a curved slender toothbrush type handle is used. Of course any type or style of handle may be used allowing for a choice of styles, configurations, and colors as desired.

In another embodiment, as seen in FIG. 8, prongs 5 and protective element 2 are molded together and are provided as one unit. Also seen is channel 11 and aperture 12 as described above.

In FIGS. 9, 10, and 11, another embodiment is shown where a multi-functioning cleat 3 is used, comprising two sides 18 and 19 with notch 8 down the middle. Preferably one side is taller, for example side 18, to assist in locating the middle notch 8. In this example, side 19 would be the longer side. Preferably, the longer side 19, has two ends 20 and 21, to facilitate changing direction of winding a strand or strands of floss around base 9 of cleat 19. Another function of such configuration is to secure a strand or strands of floss by crisscrossing them with a figure eight on side 19 of cleat 3.

As seen in FIG. 11, an embodiment is shown wherein the cleat is fabricated separately and added to the flosser to allow for increased functionality. This is accomplished with cleat 3, an extended base 9, which fits in opening 26 in handle 14, and a spring 25, is preferably inserted into opening 26 from below, followed by trigger arm 22, and plug 23, for holding the trigger arm and spring in place. Spring 25, allows trigger arm 22 to return to place after being depressed.

As is evident, a number of cleat configurations may be used with dental flossing device 10. In operation and use of the embodiments shown in FIGS. 9, 10, and 11, the cleat is preferably secured on flossing device 10, positioned away from handle 14. The post of cleat 3 preferably pierces the handle and extends below handle 14. Trigger arm 22, is preferably attached to the post of cleat 3, below the handle and extends out to one side of the device at approximately a fifteen degree angle and positioned such as to be convenient to press with either the thumb or finger. Depressing trigger arm 22 effectively rotates cleat 3 turning the notch in the top of the cleat that runs parallel to the handle, changing the angle by approximately the same thirty degrees. This process of turning the notched cleat has the effect of, when the floss is threaded around the cleat and both ends are wedged down through the notch then wrapped around several times and secured, that the floss will alternately tighten and loosen to facilitate both forcing the strand of floss between the teeth and thoroughly flossing the interdental region. In addition, when the floss is threaded around the device and one end of the floss is wedged down through the notch and the other end is wedged up through the notch then both ends are wrapped and secured, the floss will move back and forth across the span where floss is placed between the teeth when trigger arm 22 is alternately depressed and released, in effect sawing back and forth to work the floss strand into tight gaps. This second function may also be engineered and mechanized to operate by power, such as electric motor and gears 30, operably linked to cleat 3, as seen in FIG. 10, allowing for a power flosser that will operate with any and all types of readily available floss.

Another embodiment of trigger arm 22 is to incorporate a ratcheting function so that each depression of the trigger arm will advance the rotation of cleat 3 a quarter turn or so and then lock. When one end of the floss strand is secured to cleat 3, led up and across bite element 2, then back to the cleat where the strand is wrapped around many times before being secured via the notch in the cleat, each depression of the trigger will advance the strand of floss across the span of the bite piece allowing for a fresh span of floss for each gap. When done flossing the user simply continues pressing trigger 22 until the end of the floss strand is reached and the floss is taken off and thrown away.

In reference to FIGS. 9, 10, and 11, such functions are possible because of tensioning cleat 3 and trigger 22. In the embodiment illustrated, side 18 is shorter in length fore and aft but taller in height then side 19. Side 19 being longer fore and aft, tapering more to a point at ends 20 and 21, and being shorter in height. These features have the added benefit of the raised side of 18 makes it easier to find notch 8 down the middle of cleat 3 by simply passing the strand or strands of dental floss over the top of the cleat until encountering raised portion 18, then lowering the floss in notch 8. Further, the extended ends 20, 21, and one side of cleat 19, make it easier to go from wrapping the strand or strands of floss around base 9, up, over, and back down through notch 8 of cleat 3. The two extended ends 20 and 21, on cleat 3, allow for the further securing of the strands or strands of floss by criss-crossing the strand or strands of floss with a figure eight around the extended ends. These and other uses of the cleat are readily apparent from the features described.

In operation and use, dental flossing device 10, is easy to use, comfortable, reliable and efficient at flossing a users teeth. Preferably, the user simply drapes the approximate middle of a floss segment across the fingers 4 in groove 6, gathers them up, and turns the handle over and pinches the two strands together then wedges them in the cleat. Prongs 5 are gently pinched together while pulling on the floss strand until snug and then they are wrapped around cleat 3. Alternatively, a dental floss strand may be wedged in vertical slit 8 of cleat 3 and led up and over protective biting element 2 through groove 6, and through channels 7 on prongs 5, then back to the cleat. As groove 8, in cleat 3, is in line with channels 7 the use and attachment of a length of floss is very simple.

To advance a segment of floss from prong to prong across the gap over channel 11, the user simply unwinds the floss but leaves one end in the cleat slot, while the other stand is pulled down towards the handle about one inch and then both strands are pulled tight and secured.

To floss, the user simply places the span of floss between fingers 4 of the protective element in between two teeth and gently bits down on protective element 2 until the floss is pushed all the way in between the teeth. To floss deeper, the user simply bites down a little more on protective element 2, which allows the floss to penetrate deeper between the teeth. To remove the floss from between the teeth, a user simply pushes protective element 2 against the teeth opposite the flossed teeth, or if flossing the top teeth the bottom of protective element 2 is pressed, and opens his or her mouth until the floss pops out. By opening and closing the mouth several times, the same gap between teeth may be repeatably flossed.

As is evident from the above description, a wide variety of dental flossing devices may be envisioned from the device described herein and additional advantages and modifications will readily occur to those skilled in the art. The invention in its broader aspects is, therefore, not limited to the specific details, representative apparatus and illustrative examples shown and described. Accordingly, departures from such details may be made without departing from the spirit or scope of the applicant's general inventive concept.

What is claimed is:

1. A dental flossing device, comprising:
   a handle element having a forked end with spaced prongs;
   means for positioning and securing a length of floss on said handle element; and
   a soft elastomer protective bite element is oriented perpendicular to said handle and secured to said forked end of said handle, said soft elastomer protective bite element having a top surface with a notch therein sized to secure a length of dental floss, said soft elastomer protective bite element further having a channel therein.

2. The dental flossing device of claim 1, wherein said means for positioning and securing a length of floss on said handle element comprises a tensioning cleat having a vertically oriented notch therein bisecting said cleat fore and aft.

3. The dental flossing device of claim 1, wherein said handle element includes a groove therein on said spaced prongs.

4. The dental flossing device of claim 1, wherein said soft elastomer protective bite element includes a pair of spaced finger elements.

5. The dental flossing device of claim 4, wherein said soft elastomer protective bite element includes a shallow valley positioned opposite from a valley formed by said pair of spaced finger elements, to prevent a users teeth from sliding off the soft elastomer protective bite element when biting.

6. The dental flossing device of claim 1, wherein said soft elastomer protective bite element includes an aperture therein rending the protective biting element more resilient to biting.

7. The dental flossing device of claim 1, wherein said soft elastomer protective bite element is composed of a durable resilient material.

8. The dental flossing device of claim 1, wherein said soft elastomer protective bite element is composed of silicone rubber.

9. The dental flossing device of claim 1, wherein said means for positioning and securing a length of floss on said handle element comprises a tensioning cleat having a vertically oriented notch therein, wherein one half is shorter in length horizontally and taller vertically than an opposing other side, said opposing side being longer horizontally and tapering to a point in a substantially T-shape.

10. The dental flossing device of claim 9, further including a trigger arm element for rotation of said cleat when the trigger arm is depressed and released.

11. The dental flossing device of claim 10, wherein each end of a strand of floss is led to said notch from opposite ends and then secured so that when said trigger arm element is alternately depressed and released, the strand of floss will pass back and forth across a flossing span in a sawing motion to facilitate penetration between a gap between teeth.

12. The dental flossing device of claim 10, wherein each end of a strand of floss is led to said notch from opposite ends and then secured so that when said trigger arm element is alternately depressed and released, the strand of floss will pass back and forth across a flossing span in a sawing motion to facilitate penetration between a gap between teeth.

13. The dental flossing device of claim 1, further including an electrical motor and gears operably built into said handle for controlled rotation of said notched cleat.

14. A dental flossing device, comprising:
   a handle having a forked end with spaced prongs;
   means for positioning and securing a length of floss on said handle; and
   soft elastomer U-shaped protective element means for driving a length of dental floss through a space between teeth secured to said forked end of said handle, said soft elastomer protective element means having a top surface with a notch therein sized to secure a length of dental floss, and is positioned in a perpendicular orientation in relation to said handle.

15. The dental flossing device of claim 14, wherein said soft elastomer protective element means is curved element having a pair of ridges.

16. The dental flossing device of claim 14, wherein said means for positioning and securing a length of floss on said handle comprises a tensioning cleat having a vertically oriented slit therein.

17. The dental flossing device of claim 14, wherein said handle includes a dental floss receiving groove therein on said spaced prongs.

18. The dental flossing device of claim 14, wherein said soft elastomer protective element means includes a receiving notch for holding and receiving said handle.

* * * * *